United States Patent [19]

Izydore et al.

[11] Patent Number: 4,946,963

[45] Date of Patent: Aug. 7, 1990

[54] COMPOUNDS FOR THE CONTROL OF HYPERLIPIDEMIA USING N-SUBSTITUTED ISOXAZOLIDINE-3,5-DIONES

[75] Inventors: Robert A. Izydore, Durham; Iris H. Hall, Chapel Hill, both of N.C.

[73] Assignee: The University of North Carolina at Chapel Hill, Durham, N.C.

[21] Appl. No.: 264,695

[22] Filed: Oct. 31, 1988

Related U.S. Application Data

[63] Continuation-in-part of Ser. No. 119,864, Nov. 13, 1987, abandoned.

[51] Int. Cl.$^5$ .......................................... C07C 103/30
[52] U.S. Cl. ..................................................... 548/243
[58] Field of Search ........................... 514/380; 548/243

[56] References Cited

U.S. PATENT DOCUMENTS

| | | | |
|---|---|---|---|
| 3,007,936 | 11/1961 | Matter et al. | 548/243 |
| 4,256,819 | 7/1977 | Kodak | 430/41 |
| 4,302,238 | 11/1981 | Konz | 548/243 |
| 4,351,844 | 9/1982 | Patchett et al. | 514/510 |
| 4,395,417 | 7/1983 | Hall et al. | 514/372 |
| 4,499,303 | 2/1985 | Wyrick et al. | 514/605 |
| 4,504,486 | 3/1985 | Kurkov | 514/380 |
| 4,639,444 | 1/1987 | Fujikawa et al. | 514/238 |
| 4,681,893 | 7/1987 | Roth | 514/422 |

FOREIGN PATENT DOCUMENTS

| | | | |
|---|---|---|---|
| 0217035 | 9/1961 | Austria | 548/243 |
| 580263 | 7/1958 | Belgium . | |
| 1142611 | 6/1959 | Fed. Rep. of Germany | 548/243 |
| 3330602 | 8/1983 | Fed. Rep. of Germany . | |
| 1179206 | 12/1984 | Fed. Rep. of Germany . | |
| 1427602 | 7/1959 | Switzerland | 548/243 |
| 1548397 | 6/1975 | United Kingdom . | |
| 8600899 | 7/1984 | World Int. Prop. O. . | |

OTHER PUBLICATIONS

Manik Lal Debnath–"The Reaction of Benzohydroxamine . . ." 1985 Master's Thesis.
Derwent 85-080808 3/12/85 Chevron Research Co.
Manik Lak Debnath–Master's Thesis–"The Reaction of Benzohydroxamic Acids With Dicarboxylic Acid Chlorides in the Synthesis of 2,3-Benzoxazine-1,4-Diones and Isozaxzolidine-3,5-Diones" (1985).
Ronda Gayle Davis–Master's Thesis–"The Reaction of Acetone Oxime with Dicarboxylic Acid Chlorides in the Synthesis of Isoxazolidine-3, 5-Diones and 2,3–Benzoxazine-1,4-Diones" (1983).
Robert A. Izydore, Samuel McLean–Dept. of Chemistry, North Carolina Central University–Reprinted from the American Chemical Society, 97,5611(1975) "1,2-Addition Reaction of Ethyl Diazoacetate and 4–Phenyl-1,2,4-Triazoline-3,5-Dione".
Michel K. et al., Helv Chim Acta 48 (8) 1973-83 1965 CA64:12657c-h.
Rehse K., Meder J., Arch Pharm 319 (2) 133-40 1986 CA105:6446 h.
Zinner G; et al., Arch Pharm 299 (3) 222-51966 CA 64:19597d.
Zinner G. and Moll R., Arch Pharm 299 (6)562-8 1966 CA 65:10575g-h.
Ans. 40–CA 65:10575h, 1966.
Ans. 45–CA 78 (25):159531f, 1973.
Ans. 46-48–CA78(25):159531f, 1973.
Ans. 50-51–CA80(15):82760m, 1974.
Ans. 54,56-58,61,65-66–CA80(15):82760m, 1974.
Ans. 67 (1) CA104(22):186891k, 1986 (2) CA99(16):122993r, 1982.
(3) CA97(22):182935s 1982 and (4) CA87(10):68722p, 1977.
Ans. 68–CA92(21):181038m, 1980.
Ans. 72–CA93(15):149273u, 1980.
Ans. 74-77, 79-80–CA96(25):217824p, 1981.
Ans. 83 CA105(1):6446h, 1986.
Arch. Pharm. (Weiheim) 319, 133-140 (1986). Anticoagulante.

*Primary Examiner*—Mary C. Lee
*Assistant Examiner*—Catherine S. Kilby Scalzo
*Attorney, Agent, or Firm*—Cushman, Darby & Cushman

[57] ABSTRACT

An isoxazolidin-3,5-dione for the control of hyperlipidemia in mammals having the following structural formula:

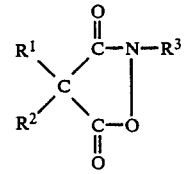

wherein $R^1$ and $R^2$ are each an alkyl of 1 to 4 carbons; $R^3$ is an alkoxybenzoyl group containing from 1 to 3 alkoxy groups wherein the alkoxy groups have from 1 to 4 carbon atoms, an alkoxybenzoyl group wherein the alkyl group had from 1 to 4 carbons, a halobenzoyl group, or a group

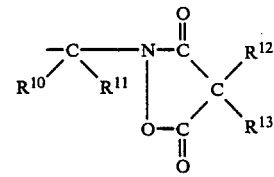

where together $R^{10}$ and $R^{11}$ form a $C_3$ to $C_7$ alkylene group, and $R^{12}$ and $R^{13}$ are each alkyl from 1 to 4 carbon atoms.

4 Claims, No Drawings

COMPOUNDS FOR THE CONTROL OF HYPERLIPIDEMIA USING N-SUBSTITUTED ISOXAZOLIDINE-3,5-DIONES

This application is a continuation-in-part of U.S. Ser. No. 119,864, filed Nov. 13, 1987, now abandoned.

BACKGROUND OF THE INVENTION

1. Field of the Invention

The present invention relates to N-substituted-isoxazolidine-3,5-diones as hypolipidemic agents and methods for their use in controlling hyperlipidemia in mammals. Specifically, the present invention is directed to methods for controlling hyperlipidemia by treating mammals, especially humans, with a class of hypolipidemic agents selected from isoxazolidine-3,5-diones.

2. Background of the Invention

Cholesterol is commonly found in all the tissues and blood of mammals, especially humans. Manufactured in the liver and other cells as a substrate for other steroids and bile acid and a component in membrane synthesis, cholesterol and its metabolic products are normal constituents of bile. As will be appreciated, many familiar foods contain cholesterol, with some containing more than others. Maintaining proper levels of cholesterol in the body has become an important factor in today's diet, since medical science has proven that certain afflictions such as hypothyroidism, diabetes and the intake of foods having a high cholesterol content may result in high levels of cholesterol in the blood with related hyperlipidemic disease states.

A condition which is associated with elevated levels of cholesterol, phospholipids, and/or triglycerides in mammals is commonly referred to as hyperlipidemia (i.e. as used herein, reference to hyperlipidemia is intended to be inclusive of both hypercholesterolemia and hypertriglyceremia, and hence, compounds having a hypolipidemic effect will exhibit activity to lower cholesterol and/or triglyceride lipid levels). Hyperlipidemia can lead to serious health problems such as artherosclerosis which may give rise to other cardiovascular disease states. Lipids occur in the blood mainly as cholesterol and triglycerides, with smaller amounts of phospholipids, fatty acids and fatty acid esters. While free fatty acids are bound to plasma albumin, the other lipids form complexes with proteins called lipoproteins. These differ in composition, size and density and include very low density lipoprotein (VLDL), low density lipoprotein (LDL) and high density lipoprotein (HDL) depending on the specific gravity of the apoprotein components of the fraction. Medical evidence points to the VLDL and LDL fractions as being associated with atherosclerosis. In contrast, the HDL fraction appears to carry cholesterol from the walls of the blood vessels to the liver where it is processed and excreted in the bile. As hyperlipidemic states increase in atherosclerosis the VLDL and LDL cholesterol increases and HDL cholesterol decreases. Effective hypolipidemic agents need to reverse this ratio since clinical data indicate that high HDL cholesterol and low LDL cholesterol protects man from myocardial infarctions. Thus, it is highly desirable to treat mammals afflicted with hyperlipidemia so as to lower cholesterol content of the VLDL and LDL fractions and increase the cholesterol content of HDL fraction.

Commercially available agents include nicotinic acid derivatives, clofibrate, cholestyramine, and cholestipol.

A number of compounds have been proposed for the treatment of hyperlipidemia in mammals. Examples include U.S. Pat. No. 4,499,303 which describes the use of a novel class of N-benzylsulfamates, N-benzoylsulfamates, and benzoylsulfonamides as useful hypolipidemic agents. U.S. Pat. No. 4,395,417 proposes the use of cyclic imides, diones, reduced diones and analogs as useful hypolipidemic agents. Also orotic acid has been shown to decrease the plasma lipid level in rats. I. H. Hall et al., *J. Pharm. Sci.*, 74, 759–64 (1985); I. H. Hall, G. H. Cocolas and W. L. Williams, Jr., *J. Pharm. Sci.*, 73, 18–20 (1984).

U.S. Pat. No. 4,639,444 describes 3,5-dialkyl-4,6-diaryltetrahydro-2H-1,3,5-thiadiazine-2-thione derivatives as useful hypolipidemic agents. U.S. Pat. No. 4,681,893 teaches that certain trans-6-[2-(3- or 4-carboxamido-substituted pyrrol-1-yl)alkyl]-4-hydroxypyran-2-ones and their ring opened acids are potent hypolipidemic agents. Likewise, U.S. Pat. No. 4,351,844 describes hypocholesterolaemic lactone compounds and their free acids which are derived from the natural fermentation product mevinolin. More recently, the control of hyperlipidemia through the use of a class of 4-pyrimidinecarboxylic acids has been described by Hall et al., *J. Pharm. Sci.* 74, 759 (1985).

In spite of the numerous compounds and methods which have been proposed for the control of hyperlipidemia, the need remains for drugs having enhanced lowering effect on levels of certain lipoprotein lipids in the serum.

Accordingly, the present invention provides a class of hypolipidemic compounds which, when administered to mammals provide for a significant increase of the cholesterol content of the HDL fraction coupled with a desirable reduction of the cholesterol of the LDL fraction. Furthermore, the triglyceride and neutral lipid content of the VLDL fraction, which carries these lipids to the tissues from the liver, are markedly reduced.

SUMMARY OF THE INVENTION

The present invention provides for a method of controlling hyperlipidemia in mammals which comprises administering to a mammal an amount effective to control hyperlipidemia of a compound having hypolipidemic activity and the structural formula:

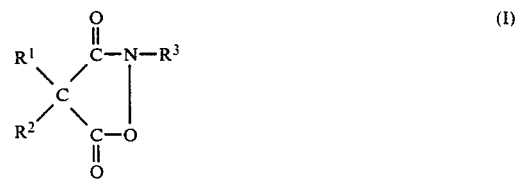

(I)

wherein $R^1$ and $R^2$, which may be the same or different provided both are not hydrogen when $R^3$ is an alkenyl or cycloalkenyl group, are selected from the group consisting of hydrogen; alkyl of 1 to 18 carbons; substituted alkyl of 1 to 18 carbons; cycloalkyl of 4 to 10 ring carbon atoms; substituted cycloalkyl of 4 to 10 ring carbon atoms; alkoxy of 1 to 8 carbon atoms; amido; carbamoyl; acyloxy; alkoxycarbonyl; halogen; aryl and substituted aryl; or together $R^1$ and $R^2$ form a $C_3$ to $C_7$ alkylene group; and $R^3$ is hydrogen; lower alkyl; substituted lower alkyl; cycloalkyl; substituted cycloalkyl; aryl; substituted aryl;

a group —COR⁴ where R⁴ is hydrogen, lower alkyl, substituted lower alkyl, cycloalkyl, substituted cycloalkyl, aryl, or substituted aryl; a group —CONHR⁵ where R⁵ has the same meaning as R⁴; an alkoxycarbonyl group —CO₂R⁶ where R⁶ has the same meaning as R⁴; an alkenyl group —CR⁷=CR⁸R⁹ where R⁷, R⁸ and R⁹, which may be the same or different, have the same meaning as R⁴; a cycloalkenyl group

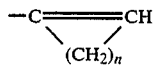

where n is an integer from 3 to 8; or a group

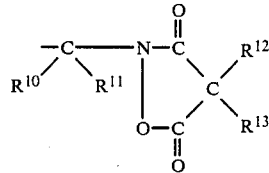

where $R^{10}$ and $R^{11}$ have the same meanings as $R^4$ or together $R^{10}$ and $R^{11}$ form a $C_3$ to $C_7$ alkylene group, and $R^{12}$ and $R^{13}$, which may be the same or different, have the same meanings as $R^1$ and $R^2$, provided that $R^1$ and $R^2$ are not both hydrogen, the pharmaceutically acceptable salts, and mixtures thereof.

In addition, the present invention provides for pharmaceutical compositions, in particular for use in controlling hyperlipidemia in mammals, which comprise, in combination with a pharmaceutically acceptable carrier, a hypolipidemically effective amount of a compound having hypolipidemic activity and a structural formula (I) as shown above and pharmaceutically acceptable salts thereof wherein R³ is a group —COR⁴ where R⁴ is hydrogen, lower alkyl, substituted lower alkyl, cycloalkyl, substituted cycloalkyl, aryl, or substituted aryl; a group —CONHR⁵ where R⁵ has the same meaning as R⁴; an alkoxycarbonyl group —CO₂R⁶ where R⁶ has the same meaning as R⁴; an alkenyl group —CR⁷=CR⁸R⁹ where R⁷, R⁸ and R⁹, which may be the same or different, have the same meaning as R⁴; a cycloalkenyl group

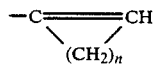

where n is an integer from 3 to 8; or a group

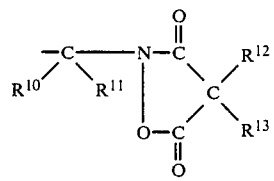

where $R^{10}$ and $R^{11}$ have the same meanings as $R^4$ or together $R^{10}$ and $R^{11}$ form a $C_3$ to $C_7$ alkylene group, and $R^{12}$ and $R^{13}$, which may be the same or different, have the same meanings as $R^1$ and $R^2$, provided that $R^1$ and $R^2$ are not both hydrogen.

A number of the isoxazolidine-3,5-dione compounds which may be used as hypolipidemic agents are new, and hence, as a further embodiment of the present invention there is provided a novel class of compounds. Specifically, isoxazolidine-3,5-diones having hypolipidemic activity and the structural formula:

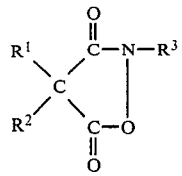

wherein

R¹ and R² are each an alkyl of 1 to 4 carbons;

R³ is an alkoxybenzoyl group containing from 1 to 3 alkoxy groups having from 1 to 4 carbon atoms, an alkylbenzoyl group wherein the alkyl group has from 1 to 4 carbons, a halobenzoyl group, or a group

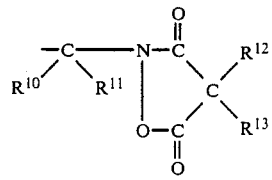

where together $R^{10}$ and $R^{11}$ form a $C_3$ to $C_7$ alkylene group, and $R^{12}$ and $R^{13}$ are each an alkyl from 1 to 4 carbon atoms, the pharmaceutically acceptable salts, and mixtures thereof. Exemplary are 1,1-bis-[2-(4,4-diethylisoxazolidine-3,5-dione)]cyclohexane; 2-(3,4,5-trimethoxybenzoyl)-4,4-diethylisoxazolidine-3,5-dione; 2-(3,4-dimethoxybenzoyl)-4,4-diethylisoxazolidine-3,5-dione; 2-(4-methoxybenzoyl)-4,4-diethylisoxazolidine-3,5-dione; 2-(4-methylbenzoyl)-4,4-diethylisoxazolidine-3,5-dione; and 2-(4-chlorobenzoyl)-4,4-diethylisoxazolidine-3,5-dione. Preferably, the compound is 2-(3,4,5-trimethoxybenzoyl)-4,4-diethylisoxazolidine-3,5-dione; 2-(4-methylbenzoyl)-4,4-diethylisoxazolidine-3,5-dione; or 2-(4-chlorobenzoyl)-4,4-diethylisoxazolidine-3,5-dione.

As referred to herein, "hypolipidemic activity" refers to the ability of the compounds of formula (I) to lower levels of cholesterol and/or triglycerides in mammals to which the compound is administered, in particular, levels in serum and in blood vessel walls such as the aortic walls.

The synthesis of a number of the isoxazolidine-3,5,-diones has been described in the literature. For example, the synthesis of N-benzoyl-4,4-diethylisoxazolidine-3,5-dione has been described by G. Zinner and R. Moll, Arch. Pharm., 299, (6), 562–8 (1966) CA 65:10575f. Likewise, N-acetylisoxazolidine-3,5-dione has been studied with regard to its polymerization. A. B. Richon et al, J. Med. Chem. 25, (6) 745–7 (1982) (Ring 33241X) and K. Rehse et al, Arch. Pharm. 319, (2) 133–40, (1986) (Ring 86-30095) discuss isoxazolidine-3,5-diones lacking a N-acyl substituent as aldose reductase inhibitors and anticoagulants, respectively. However, no suggestion has been made in this literature reference with regard to any hypolipidemic activity of the isoxazolidine-3,5-dione compounds.

DETAILED DESCRIPTION OF THE INVENTION

We have found that the isoxazolidine-3,5-dione compounds of formula (I) above effectively lower serum and aortic wall lipids in mammals. The term mammals as used herein is intended in its normal sense, and hence is inclusive of not only mice, rats, dogs, cats, horses, pigs, sheep, cows and other animals, but humans as well. Through the use of the hypolipidemic agents of the present invention, we observed the inhibition of activity of the rate limiting enzyme of cholesterol synthesis (HMG CoA reductase) as well as the lowering of serum levels of the acyl CoA cholesterol acyl transferase (cholesterol ester), acetyl CoA carboxylase (fatty acid), sn glycerol-3-phosphate acyl transferase and phosphatidylate phosphohydrolase (triglyceride) and heparin induced membrane bound lipoprotein lipase (plasma).

The hypolipidemic isoxazolidinediones of the present invention afford reduction in both serum cholesterol and triglyceride levels and in aortic wall cholesterol and can be used in lower dosage amounts than commercially available hypolipidemic agents such as nicotinic acid derivatives, clofibrate, cholestyramine and cholestipol. Through the use of the isoxazolidinedione agents of the present invention we have observed significant increases in HDL-cholesterol levels and reduced levels of VLDL and LDL cholesterol with an acceleration of lipid excretion in the bile via the feces.

As used herein, the terms "lower alkyl" and "lower alkoxy" are intended to refer to substituents of 1 to 8 carbons and may be straight chain or branched. Preferred alkyl groups include methyl, ethyl, n-propyl, iso-propyl, n-butyl or t-butyl, and are more preferably methyl or ethyl; and preferred alkoxy include methoxy, ethoxy, propoxy, or butoxy, and are more preferably methoxy.

Exemplary of suitable cycloalkyl groups are cyclobutyl, cyclopentyl or cyclohexyl, and is preferably cyclohexyl.

The terms "substituted alkyl" and "substituted cycloalkyl" are intended to refer to alkyl groups with at least one substituent wherein the alkyl group has 1 to 8 carbons and cycloalkyl groups substituted with at least one substituent wherein the cycloalkyl group has 4 to 10 carbon atoms. Substituents include, for example, alkyl, alkoxy, oxo, alkoxycarbonyl, halogen, nitro, aryl, carbamoyl, amino, amido, acyloxy, hydroxy, carboxy, alkylthio, sulfoxide, sulfone, thiol, sulfonyl, sulfano, phosphono and silyl.

As used herein, the term "aryl" is intended to include an aromatic group containing 4 to 14 carbon atoms and optionally containing one or more heteroatoms selected from —O—, —S—, and —N—. Examples include phenyl, naphthyl, pyridyl, pyrimidinyl, pyrazinyl, triazinyl, thiazolyl, quinolinyl, benzimidazolyl, benzothiazolyl, or benzoxazolyl. A preferred aryl group is phenyl.

The term "substituted aryl" refers to the presence on the aromatic ring of at least one substituent. Substituents include, for example, lower alkyl, substituted lower alkyl, lower alkoxy, acyl, alkoxycarbonyl, halogen, nitro, carbamoyl, amino, amido, acyloxy, hydroxy, carboxy, alkylthio, sulfoxide, sulfone, thiol, sulfonyl, sulfano, phosphono and silyl.

"Halogen" and the prefix "halo" includes bromine, chlorine, fluorine and iodine atoms, and is preferably a chlorine or bromine atom.

As used herein, the term "amido" includes a group containing 1 to 12 carbon atoms. Exemplary are formamido, acetoamido, propionamido, benzamido, furamido, phenylacetamido, and substituted derivatives thereof, such as chloracetamido, trifluoracetamido and nitrobenzamido.

The term "carbamoyl" includes a group of formula —$CONR^{14}R^{15}$ wherein $R^{14}$ and $R^{15}$ are each hydrogen, lower alkyl as defined above, aryl as defined above or, together with the nitrogen atom, form a saturated heterocyclic amino group which has 5 to 7 membered ring, optionally containing in the ring one or more atoms selected from the group consisting of —O—, —S—, —NH—, and —N(CH$_3$)—.

As used herein, the term "acyloxy" is intended to include a group of formula $R^{16}COO$— wherein $R^{16}$ includes a hydrogen atom or an optionally substituted lower alkyl, cycloalkyl or aryl group.

The term "alkenyl" refers to groups having at least one double bond and includes cycloalkenyl and the group —$CR^7$=$CR^8R^9$, wherein $R^7$, $R^8$ and $R^9$ are hydrogen, lower alkyl, substituted lower alkyl, cycloalkyl, substituted cycloalkyl, aryl, or substituted aryl.

Preferred compounds from within the class defined by formula (I) are those where $R^1$ and $R^2$ are the same and are lower alkyl, preferably $C_1$ to $C_6$ alkyl, and most especially ethyl.

An especially preferred class of hypolipidemic agents are the 2-benzoyl-4,4-dialkylisoxazolidine-3,5-dione compounds where the phenyl ring may preferably be substituted with one or more lower alkyl or lower alkoxy substituents or halogen atoms. Preferred compounds include those where $R^4$ in the group —$COR^4$ is trimethoxyphenyl, dimethoxyphenyl, methoxyphenyl, methylphenyl, chlorophenyl or phenyl.

Yet another group of preferred compounds include those where $R^3$ is an alkenyl substituent —$CR^7$=$CR^8R^9$, where $R^7$ is methyl or phenyl and $R^8$ and $R^9$ are both hydrogen.

Thus, within the class of agents depicted by formula (I) the following compounds are contemplated agents:

2-(2-propenyl)-4,4-diethylisoxazolidine-3,5-dione;
2-(2-propenyl)-4,4-dimethylisoxazolidine-3,5-dione;
2-(2-butenyl)-4-ethylisoxazolidine-3,5-dione;
2-(2-propenyl)-4,4-diphenylisoxazolidine-3,5-dione;
2-(1-phenylethenyl)-4,4-diethylisoxazolidine-3,5-dione;
2-(1-phenylethenyl)-4,4-di(3-chloropropyl)isoxazolidine-3,5-dione;
2-(1-phenethenyl)-4,4-dimethylisoxazolidine-3,5-dione;
1,1-bis-[2-(4,4-diethylisoxazolidine-3,5-dione)]cyclohexane;
1,1-bis-[2-(4,4-dimethylisoxazolidine-3,5-dione)]cyclo-hexane;
2-(3,4,5-trimethoxybenzoyl)-4,4-diethylisoxazolidine-3,5-dione;
2-(3,4,5-trimethoxybenzoyl)-4,4-dimethylsioxazolidine-3,5-dione;
2-(3,4-dimethoxybenzoyl)-4,4-diethylisoxazolidine-3,5-dione;
2-(3,4-dimethoxybenzoyl)-4,4-dimethylisoxazolidine-3,5-dione;
2-benzoyl-4,4-diethylisoxazolidine-3,5-dione;
2,2-bis-[2-(4,4-diethylisoxazolidine-3,5-dione)]-propane;
2-(4-methoxybenzoyl)-4,4-diethylisoxazolidine-3,5-dione;

2-(4-methylbenzoyl)-4,4-diethylisoxazolidine-3,5-dione; and 2-(4-chlorobenzoyl)-4,4-diethylisoxazolidine-3,5-dione.

For those compounds of Formula (I) which can be converted into pharmaceutically acceptable salts, the salts may be used. These salts may be acid addition salts formed from inorganic or organic acids, e.g. hydrochlorides, sulfates, phosphates, benzoates or acetates, or salts formed with bases, e.g. alkali metal salts such as sodium or potassium salts.

The amount of hypolipidemically active compound as defined by Formula (I) which is required for the treatment of patients suffering from elevated lipid levels will vary with the route of administration, the condition of the patient under treatment and is ultimately at the discretion of the attending physician. However, a suitable dose of the active compound is in the range of from about 1 to about 100 mg/kg body weight per day; preferably from about 4 to about 16 mg/kg daily. Thus, for example, when administered to man (of approximately 70 kg body weight) in multiple daily doses, e.g. four times daily, a typical unit or sub-dose of the active compound is about 150 mg.

The form of the dose is not critical and may be formulated for oral, buccal, parenteral or rectal administration or in a form suitable for administration by inhalation or insufflation. Oral administration of the agent is preferred.

Tablets and capsules for oral administration may contain conventional excipients such as binding agents, for example mucilage of starch or polyvinylpyrrolidone; fillers, for example, lactose, microcrystalline cellulose or cornstarch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art.

Oral liquid preparations may be in the form of, for example, aqueous or oily suspensions, solutions, emulsions, syrups or elixirs, or may be presented as a dry product for constitution with water or another suitable vehicle before use. Such liquid preparations may contain conventional additives such as suspending agents, for example, sorbitol syrup, methyl cellulose, glucose/sugar syrup or carboxymethyl cellulose; emulsifying agents, for example, sorbitan mono-oleate; non-aqueous vehicles (which may include edible oils), for example, propylene glycol or ethyl alcohol; and preservatives, for example, methyl or propyl p-hydroxybenzoates or sorbic acid. Suitably, a 1% aqueous solution of carboxymethylcellulose may be employed.

The compound of formula (I), or its pharmaceutically acceptable salts, may also be formulated as suppositories, e.g. containing conventional suppository bases such as cocoa butter or other glycerides.

For buccal administration, the composition may take the form of tablets or lozenges formulated in conventional manner.

The compound of formula (I) and its physiologically acceptable acid addition salts may be formulated for parenteral administration by injection or continuous infusion and may be presented in unit dose form in ampoules, or in multi-dose forms with an added preservative.

The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g. sterile, pyrogen-free water, before use.

It will therefore be appreciated that the compounds of formula (I), or their pharmaceutically acceptable salts, may be used in the manufacture of a medicament for the treatment of human or animal subjects suffering from hyperlipidemia.

Isoxazolidine-3,5-diones substituted at position 2 are cyclic N-substituted analogs of hydroxamic acids. They are generally prepared by the reaction of N-substituted hydroxylamines with either malonyl chlorides in the presence of an organic base or malonate esters.

Accordingly, the compounds of formula (I) and pharmaceutically acceptable salts thereof may be prepared as described below.

According to the general process (A), compounds of the formula (II)

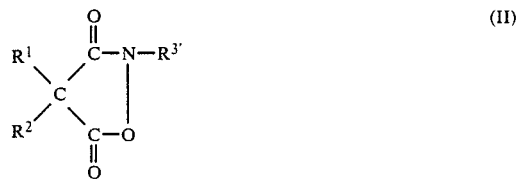

wherein $R^1$ and $R^2$ are as defined above and $R^{3'}$ is the same as $R^3$ except that $R^{3'}$ does not represent —CONHR$^5$ or CO$_2$R$^6$ where R$^5$ and R$^6$ have the same meaning as R$^4$, or a group —CR$^7$=CR$^8$R$^9$ wherein R$^7$, R$^8$ and R$^9$ are as defined above, or a group:

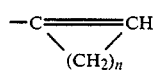

wherein n is defined as above, or a group:

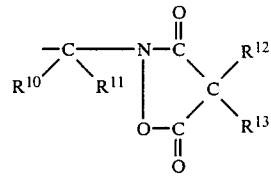

wherein $R^{10}$, $R^{11}$, $R^{12}$ and $R^{13}$ are as defined above, may be prepared by reacting a compound of formula (III):

wherein each of $X^1$ and $X^2$, which may be the same or different, is a readily displaceable atom or group such as a halogen atom, e.g. chlorine or bromine, or an alkoxy group, e.g. methoxy or ethoxy, and $R^1$ and $R^2$ are as defined above, with a compound of formula (IV):

wherein R$^{3'}$ is as defined above.

The reaction is preferably carried out in the presence of an organic base, e.g. a tertiary organic base such as a tri-(loweralkyl)amine (e.g. triethylamine), or pyridine. The base may be used in excess (for example, 50% molar excess relative to the compound of formula (III)).

It is desirable that the reaction be carried out in a solvent or solvent mixture, for example, one selected from hydrocarbons (e.g. cyclohexane) halogenated hydrocarbons (e.g. methylene chloride), ethers (e.g. diethyl ether), or mixtures of these solvents. A particularly preferred solvent is diethyl ether.

The reaction conveniently may be carried out at a temperature of between −10° C. and the boiling temperature of the reaction mixture, for example in the range −10° C. to +80° C.

According to a further aspect of the invention, we provide a process (B) in which compounds of the general formula (II), wherein R$^1$, R$^2$ and R$^{3'}$ are defined as above, except that additionally R$^{3'}$ does not represent hydrogen, aryl or substituted aryl are formed by reacting a compound of formula (V):

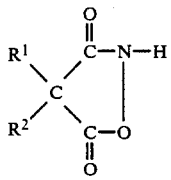 (V)

wherein R$^1$ and R$^2$ are as defined above, with a compound of formula (VI):

 (VI)

wherein R$^5$ is as defined above, in the presence of a suitable base; or with a compound of formula (VII):

 (VII)

wherein R$^6$ has the same meaning as R$^4$ and Z is a readily displaceable atom or group such as a halogen, e.g. chloride or bromide, in the presence of a suitable base.

Compounds of formula (V) are prepared as previously described by reacting a compound of formula (III) wherein X$^1$, X$^2$m R$^1$ and R$^2$ are as defined above, with a compound of formula (VIII):

 (VIII)

or a suitable acid salt of formula (VIII). The reaction is preferably carried out in the presence of a suitable base, such as pyridine.

According to another aspect of the invention, there is a process (C) in which compounds of the general formula (I), wherein R$^3$ represents a group:

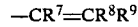

wherein R$^7$, R$^8$ and R$^9$ are as defined above, are formed by the method of process (A) described above by the reaction of a compound of formula (III), as defined above and provided that R$^1$ and R$^2$ are not both hydrogen, with a compound of formula (IX):

 (IX)

wherein R$^7$, R$^8$ and R$^9$ are as defined above, in an excess of base (e.g. 50% molar excess relative to the compound of formula (III).

According to a still further aspect of the invention, there is provided a process (D) in which the compounds of general formula (I), wherein R$^3$ represents a group:

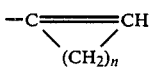

wherein n is as defined above, are formed by the method of general process (A) described above by the reaction of a compound of formula (III), as defined above and provided that R$^1$ and R$^2$ are not both hydrogen, with a compound of formula (X):

 (X)

wherein n is as defined above, in a stoichiometric amount of a suitable base (e.g. relative to the compound of formula (III)).

According to a still further aspect of the invention, there is a process (E) in which compounds of general formula (I), wherein R$^3$ represents a group:

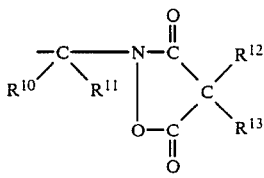

wherein R$^{10}$, R$^{11}$, R$^{12}$ and R$^{13}$ are as defined above, are formed by the reaction of general process (A) by the reaction of a compound of formula (III), as defined above and provided that R$^1$ and R$^2$ are not both hydrogen, with a compound of formula (IX), as defined above, or with a compound of formula (X), as defined above, in an excess of a suitable base (e.g. 50% molar excess relative to the compound of formula (III)).

Compounds of formulae (III), (IV), (VI), (VII), (VIII), (IX) and (X) are well known in the art, either being commercially available or their preparation having been previously described.

The reaction product may be separated from the reaction mixture which may contain, for example, products of minor cross-reactions, by a variety of conventional separation procedures including extraction with acids and/or bases, recrystallization, column chromatography and high-performance liquid chromatography (HPLC).

Pharmaceutically acceptable salts of a number of the compounds of general formula (I) may be prepared by reacting a compound of general formula (I) with an appropriate acid or base in the presence of a suitable solvent such as acetonitrile, acetone, choloroform, ethyl acetate or an alcohol, e.g. methanol, ethanol or isopropanol.

Pharmaceutically acceptable salts may also be prepared from other salts, including other pharmaceutically acceptable salts of certain compounds of general formula (I), using conventional methods.

Reaction Products of Acetone Oxime with Dialkylmalonyl Chlorides

Acetone oxime reacted with dialkylmalonyl chlorides, which included dimethylmalonyl chloride and diethylmalonyl chloride, in the presence of triethylamine at 0° C. to give as products 2-(2-propenyl)isoxazolidine-3,5-diones including 2-(2-propenyl)-4,4-dimethylisoxazolidine-3,5-dione (4a) and 2-(2-propenyl)-4,4-diethylisoxazolidine-3,5-dione (4b), and 2,2-bis-[2-(isoxazolidine-3,5-dione)]propanes, including 2,2-bis-[2-(4,4-dimethylisoxazolidine-3,5-dione)]propane (5a) and 2,2-bis-[2-(4,4-diethylisoxazolidine-3,5-dione)]propane (5b). Formed as minor products were 4,4-dimethylisoxazolidine-3,5-dione (6a), and 4,4-diethylisoxazolidine-3,5-dione. Table I lists the percent yield data for the products that were isolated. The present yields of both 4b and 5b were significantly increased when the reaction between acetone oxime and diethylmalonyl chloride was carried out in the presence of excess triethylamine.

TABLE I

Products Isolated from the Reaction of Acetone Oxime with Dialkylmalonyl Chlorides

| product | yield, % |
|---|---|
| 4a | 13[a] |
| 4b | 6[a] |
|   | 23[b] |
| 5a | 21[a] |
| 5b | 22[a] |
|   | 51[b] |
| 6a | 2[a] |

[a]The reaction was carried out with a stoichimetric quantity of triethylamine.
[b]The reaction was carried out with a 50% excess of triethylamine.

The structures of the 2-(2-propenyl)isoxazolidine-3,5-diones and 2,2-bis-[(2-isoxazolidine-3,5-dione)]propanes followed from their spectral and elemental analyses data. The 2-(2-propenyl)isoxazolidine-3,5-diones gave abundant MS molecular ion peaks. The 2,2-bis-[2-(isoxazolidine-3,5-dione)]propanes did not show MS molecular ion peaks but showed instead in the high mass region peaks resulting from alpha-cleavage of an isoxazolidine-3,5-dione radical from the central carbon atoms of the molecular ions. The UV spectral data for 4a and 4b represent the first reported UV data for isoxazolidine-3,5-diones. The compounds absorbed at λ max (acetonitrile) 222 nm and 223 nm, respectively.

Compound 6a was isolated as a white crystalline solid. It has been previously reported. 4,4-Diethylisoxazolidine-3,5-dione was obtained in low yield as part of a mixture with 5b. Its presence in the mixture was indicated by mass spectrometry which showed m/z 157.0737 (M+) and by $^1$H NMR spectroscopy which showed its NH bond as a broad singlet at δ9–10. Extraction of a methylene chloride solution of the mixture with aqueous sodium carbonate caused the NH peak of 4,4-diethylisoxazolidine-3,5-dione to be removed from the $^1$H NMR spectrum.

EXPERIMENTAL

Melting points and boiling points are uncorrected. Infrared spectra were recorded on a Beckman Acculab 10 spectrophotometer. Ultraviolet spectra were obtained on a Beckman DBG spectrophotometer. $^1$H NMR spectra were recorded on a Varian EM-360A spectrometer. Mass spectra were determined on an AEI-902 mass spectrometer at the Research Triangle Institute of Mass Spectrometry, Research Triangle Park, N.C., U.S.A.; Elemental analyses were performed by Integral Microanalytical Laboratories, Raleigh, N.C. Acetone oxime, diethylmalonyl chloride, and malonyl chloride were purchased commercially. Dimethylmalonyl chloride was prepared by the procedure of S. B. Speck, *J. Am. Chem. Soc.*, 74 2876 (1952). Ethyl ether was dried by distillation over lithium aluminum hydride.

The following examples are provided to more fully illustrate the invention, but are not to be construed as limiting the scope thereof.

EXAMPLE 1

Preparation of 2-(2-propenyl)-4,4-diethyl-isoxazolidine-3,5-dione and 2,2-bis-[2-(4,4-diethylisoxazolidine-3,5-dione)]1 propane: General Procedure for the Reaction of Acetone Oxime with Malonyl Chlorides A solution containing 3.65 g (5.00 mmole) of acetone oxime and 15.0 mmole of triethylamine in 150 ml of dry ethyl ether was cooled to 0°–5° C. with stirring. A solution of 5.00 mmole of the malonyl chloride in dry ethyl ether was added dropwise over 1 hour. Stirring was continued for 1 hour at 0°–5° C. The precipitate of triethylamine hydrochloride was removed by filtration, and the filtrate was concentrated in vacuo to yield the product residue. The ether filtrate was washed with 10% hydrochloric acid to remove the excess triethylamine and dried over anhydrous magnesium sulfate prior to concentration.

A. Reaction of Acetone Oxime with Dimethymalonyl Chloride

The crude product was prepared by the general procedure described above. The product residue was heated in 65 ml of hot cyclohexane. The hot solution was decanted from an insoluble oil and cooled in the freezer. The white precipitate was removed by filtration and heated in 15 ml of petroleum ether. The insoluble solid was filtered to give 2% of 4,4-dimethylisoxazolidine-3,5-dione (6a) as a white solid, mp 106°–109° C.; G. Zinner, H. Ruthe, and D. Bose, *Pharmazie*, 29, 16 (1974); $^1$H NMR (deuterioacetone): δ9.45 (br s, 1H), 1.44 (s, 6H); mass spectrum m/z. Calc'd for: $C_5H_7NO_3$: 129.0425. Found: 129.0428. The petroleum ether filtrate was cooled and filtered to remove pure 2,2-bis-(4,4-dimethylisoxazolidine-3,5-dione)propane (5a) as white crystals, mp 114°–116°; IR (nujol): 1830, 1760 (s), 1710 (s) cm$^{-1}$; UV (acetonitrile): λ max 222 nm (ε5200); $^1$H NMR (deuteriochloroform): δ2.33 (s, 6H), 1.73 (s, 12H); mass spectrum m/z. Calc'd for: $C_8H_{12}NO_3$ (M—$C_5H_6NO_3$): 170.0816. Found: 170.0816. *Elemental Analysis:* Calc'd for: $C_{13}H_{18}N_2O_6$: C, 52.35; H, 6.08; N, 9.39. Found: C, 52.13; H, 6.05; N, 9.37.

The petroleum ether filtrate was evaporated in vacuo to give a small quantity of viscous liquid containing 5a and dimethylketoximyl dimethylmalonate: $^1$H NMR (deuteriochlorform): δ2.33(s), 2.00(s), 1.92(s), 1.73 (s). Treatment with a few ml of petroleum ether dissolved most of the viscous liquid. The mixture was filtered to remove a small quantity of 5a and concentrated in vacuo. The process was repeated. Integration of the $^1$H nmr spectrum of the resulting viscous liquid indicated the presence of approximately 50% each of 5a and dimethylketoximyl dimethylmalonate. The cyclohexane filtrate was concentrated in vacuo to a yellow viscous liquid. Distillation of the liquid gave 13% of 2-(2-propenyl)-4,4-dimethylisoxazolidine-3,5-dione (4a) as a colorless liquid, bp 51°–72° C. (0.40 torr). Redistillation gave analytically pure 4a, bp 55°–57° C. (0.35 torr); IR (neat): 1830 (s), 1735 (s) cm$^{-1}$; UV (acetonitrile): λmax 258 nm (ε7320), 226 (ε7200); $^1$H NMR (deuteriochloroform): δ4.9 (s, 1H), 4.1 (s, 1H), 2.15 (s, 3H), 1.4 (s, 6H); mass spectrum m/z (rel. intensity): 169 (89) M$^+$, 70 (97) Me$_2$C=C=O$^+$, 55 (100). *Elemental Analysis:* Calc'd for: C$_8$H$_{11}$NO$_3$: 56.79; H, 6.56; N, 8.28. Found: C, 56.55; H, 6.72; N, 8.11.

B. Reaction of Acetone Oxime with Diethylmalonyl Chloride In the Presence of a Stoichiometric Quantity of Triethylamine The crude product was prepared by the general procedure described above. The viscous product residue was distilled under reduced pressure to give a fraction, bp 64°–79° C. (0.30 torr), and a fraction, bp 75°–106° C. (0.30 torr). The higher the boiling fraction solidified on standing. It was recrystallized from petroleum ether to give 2,2-bis-[2-(4,4-diethylisoxazolidine-3,5-dione)]propane (5b) as a white solid, mp 78°–80°; IR (Nujol): 1845 (s),1740 (s) cm$^{-1}$; UV (acetonitrile): max 223 nm (ε8540); $^1$H NMR (deuteriochloroform): δ2.1 (s, 6H), 1.9 (q, 8H), 0.9 (t, 12H); mass spectrum m/z. Calc'd for: C$_{10}$H$_{16}$NO$_3$ (M—C$_7$H$_{10}$NO$_3$): 198.1129. Found: 198.1133. Elemental Analysis: Calc'd for: C$_{17}$H$_{26}$N$_2$O$_6$: C, 57,61; H, 7.39; N, 7.90. Found: 57.31; H, 7.46; N, 7.71.

The lower boiling fraction was redistilled to give analytically pure 2-(2-propenyl)-4,4-diethylisoxazolidine-3,5-dione (4b), bp 64°14 66° (0.30 torr); IR (neat): 1830 (s), 1740 (s), 1655 (m) cm$^{-1}$; UV (acetonitrile): λmax 226 nm (ε6840), 250 (ε5120); $^1$H NMR (deuteriochloroform): δ5.0 (s, 1H), 4.6 (s 1H), 2.22 (s, 3H), 1.9 (q, 4H), 0.80 (t, 6H); mass spectrum m/z (rel. intensity): 197 (82) M$^+$, 98 (39) (Et$_2$C=C=O$^+$), 55 (100). *Elemental Analysis:* Calc'd for C$_{10}$H$_{15}$NO$_3$: C, 60.90; H, 7.66; N, 7.10. Found: C, 60.86; H, 7.88; N, 7.32.

C. Reaction of Acetone Oxime with Diethylmalonyl Chloride In the Presence of Excess Triethylamine The viscous product residue was distilled under reduced pressure to yield 4b, bp 65°–68° C. (0.32 torr), and a fraction, bp 71°–118° C. (0.32 torr) which solidified on standing. The solidified fraction was heated in petroleum ether. A small quantity of an insoluble solid containing 4,4-diethyisoxazolidine-3,5-dione was removed by filtration; $^1$H NMR (deuterioacetone): δ9–10 (br s); mass spectrum m/z. Calc'd for: C$_7$H$_{11}$NO$_3$: 157.0738. Found: 157.0737. The petroleum ether filtrate was cooled and filtered to yield pure 5b, mp 78°–80° C. The petroleum ether filtrate was concentrated in vacuo to give a small quantity of a viscous liquid containing 5b and dimethylketoximyl diethylmalonate; $^1$H NMR (deuteriochloroform): δ2.10 (s), 2.00 (s), 1.92 (s), 1.9 (m), 0.9 (m). The viscous liquid was treated two times with petroleum ether as described for dimethylketoximyl diethylmalonate. Integration of the resulting $^1$H nmr spectrum indicated the presence of approximately 50% each of 5b and the dimethylketoximyl diethylmalonate.

EXAMPLE 2

Preparation of 2-(3,4,5-trimethoxybenzoyl)-4,4-diethylisoxazolidine-3.5-dione

A mixture consisting of 2.27 g (0.0100 mol) of 3,4,5-trimethoxybenzohydroxamic acid (recrystalized from absolute ethanol prior to the reaction), 5 ml of pyridine, and 100 ml of methylene chloride was prepared in a 250 ml round-bottom flask. The mixture was cooled in an ice bath, and 2.00 g (0.0101 mol) of diethylmalonyl chloride was added dropwise over a 15 minute period. The reaction mixture was stirred for one hour at room temperature after which time all of the hydroxamic acid had dissolved. The solution was extracted three times with 50 ml portions of water, four times 50 ml portions of 5% hydrochloric acid, and two times with 50 ml portions of 5% sodium carbonate. The methylene chloride solution was dried (MgSO$_4$) and evaporated to dryness under reduced pressure to give 2.86 g (81.5%) of crude 2-(3,4,5-trimethoxybenzoyl)-4,4-diethylisoxazolidine-3,5-dione as a solid residue: mp 103°–106° C. Recrystallization of 2.72 g of the crude product from 20 ml of absolute ethanol gave 2.14 g of 2-(3,4,5-trimethoxybenzoyl)-4,4-diethylisoxazolidine-3,5-dione: mp 107°–109.5° C.

Purification of 2-(3,4,5-Trimethoxybenzoyl)-4,4-diethylisoxazolidine-3,5-dione by Flash Chromatography A sample of 2-(3,4,5-trimethoxybenzoyl)-4,4-diethylisoxazolidine-3,5-dione (96.8% purity by HPLC) weighing 1.00 g was dissolved in two ml of HPLC grade ethyl acetate. The resulting solution was placed on a 38.7 cm×11.0 cm (O.D.) chromatography column containing 200–425 mesh (type 60)Å silica gel as the adsorbant. The developing solvent was eluted through the column under an external pressure of 5 psig which was obtained with the use of a cylinder of nitrogen gas. Fifteen fractions were collected in 100 ml increments. The following fractions were collected from the column with the indicated solvent systems: 1–10 (hexane:ethyl acetate, 70:30) and 11–15 (hexane:ethyl acetate, 50:50). Each fraction was analyzed by HPLC on a silica gel column using a solvent system of hexane:ethyl acetate (1:99). Based on the HPLC data, fractions 5–10 were combined and evaporated under reduced pressure. A portion of the solid residue from the combined fractions 5–10 weighing 0.79 g was recrystallized from 15 ml of absolute ethanol to yield 0.71 g of pure 2-(3,4,5-trimethoxybenzoyl)-4,4-diethylisoxazolidine-3,5-dione as a white solid: mp 107°–108° C.; IR (Nujol) 1802 (s, C=O), 1755 (s, C=O), 1692 (s, C=O), 1580 (s), and 708 cm$^{-1}$ (m, aromatic C—H bend), $^1$H NMR (60 MHz, CDCl$_3$) δ7.02 (s, 2, aromatic C—H), 3.85 (overlapping singlets, 9, OCH$_3$), 2.07 (q, 4, C—CH$_2$), and 1.01 (t, 6, CH$_3$); high resolution MS Calc'd for: C$_{17}$H$_{21}$NO$_7$: 351.1318. Found: 351.1319; MS m/z (rel. intensity) 351 (9, M$^+$), 307, (4, M—CO$_2$), 195 (100). *Elemental Analysis:* Calc'd for: C$_{17}$H$_{21}$NO$_7$; C, 58.11; H, 6.03; N, 3.99. Found: C, 58.11; H, 6.09; N, 3.96.

EXAMPLE 3

Preparation of 2-Benzoyl-4,4-diethylisoxazolidine-3,5-dione

A mixture consisting of 1.37 g (0.0100 mol) of benzohydroxamic acid, 10 ml of pyridine, and 100 ml of methylene chloride was prepared in a 250 ml round-bottom flask. The mixture was cooled in an ice bath and 2.00 g (0.101 mol) of diethylmalonyl chloride was added dropwise over a 15 minute period. The reaction mixture was stirred for one hour at room temperature after which time all the benzohydroxamic acid had dissolved. The solution was evaporated under reduced pressure, and to the residue was added 100 ml of cold water. The insoluble viscous oil was rubbed with a glass rod to effect solidification. The solid was filtered and dried to give 1.89 g (75.9%) of crude 2-benzoyl-4,4-diethylisoxazolidine-3,5-dione: mp 76°-79° C. Recrystallization of 1.72 g of crude isoxazolidine-3,5-dione from 20 ml of absolute ethanol gave 1.56 g of pure 2-benzoyl-4,4-diethylisoxazolidine-3,5-dione: mp 87°-88° C. (lit 87°-88° C.) G. Zinner and R. Moll, Arch. Pharm., 299, (6), 562-8(1966), CA 65 10575f; IR (Nujol) 1817 (s, C=O), 1762 (s, C=O), 1714 (s, C=O) and 694 (s, aromatic C—H bend) cm$^{-1}$: NMR (acetone-d$_6$) δ7.46 (m, 5, aromatic C—H), 1.87 (q, 4, CH$_2$), 1.00 (t, 6, CH$_3$).

EXAMPLE 4

Preparation of 2-(4-Methoxybenzoyl)-4,4-diethylisoxazolidine-3,5-dione

A mixture consisting of 1.67 g (0.0107 mol) of 4-methoxybenzohydroxamic acid, mp 158°-15920 C. (dec.)(lit. mp 156°-157° C. (dec.), Beilstein Handbook of Organic Chemistry, series H, vol 10, p. 170), 5 ml of pyridine, and 100 ml of methylene chloride was prepared in a 250 ml round bottom flask. The mixture was cooled in an ice bath, and 2.107 g (0.0107 mol) of diethylmalonyl chloride was added dropwise over a 15 minute period with stirring. The reaction mixture was stirred for 2 hours at room temperature after which time all the hydroxamic acid had dissolved. The solution was extracted two times with 50 ml portions of water, three times with 50 ml portions of 5% hydrochloric acid, and two times with 50 ml portions of 5% sodium carbonate. The methylene chloride was dried (MgSO$_4$) and evaporated to dryness under reduced pressure to give 2.19 g (70.4%) of crude 2-(4-methoxybenzoyl)-4,4-diethylisoxazolidine-3,5-dione as a solid residue. Recrystallization of the solid from absolute ethanol gave pure 2-(4-methoxybenzoyl)-4,4-diethylisoxazolidine-3,5-dione as a white solid: mp 116°-118° C.; IR (Nujol) 1810 (s,C=O), 1750 (s, C=O), 1690 cm$^{-1}$ (s, C=O); $^1$H NMR (400 MHz, CDCl$_3$) 7.83 (d, 2H), 6.98 (d, 2H), 3.89 (t, 3H), 1.95 (q, 4H), 1.01 (t, 6H); High resolution MS, calc'd for: C$_{15}$H$_{17}$NO$_5$: 291.1102. Found: 291.1106. Anal. Calc'd for: C$_{15}$H$_{17}$NO$_5$: C, 61.84; H, 5.88; N, 4.81. Found: C, 61.83; H, 5.76; N, 4.76.

EXAMPLE 5

Preparation of 2-(4-Methylbenzoyl)-4,4-diethylisoxazolidine-3,5-dione

A mixture consisting of 1.51 g (0.0100 mol) of 4-methylbenzohydroxamic acid, mp 148°-150° C. (dec.) (lit. mp 148° C. dec., Beilstein Handbook of Organic Chemistry, series H, vol 9, p. 491), 5 ml of pyridine, and 100 ml of methylene chloride was prepared in a 250 ml round bottom flask. The mixture was cooled in an ice bath, and 1.977 g (0.0100 mol) of diethylmalonyl chloride was added dropwise over a 15 minute period with stirring. The reaction mixture was stirred for 2 hours at room temperature after which time all the hydroxamic acid had dissolved. The solution was extracted two times with 50 mL portions of water, three times with 50 mL portions of 5% hydrochloric acid, and two times with 50 mL portions of 5% sodium carbonate. The methylene chloride was dried (MgSO$_4$) and evaporated to dryness under reduced pressure to give 0.94 g (34.2%) of crude 2-(4-methylbenzoyl)4,4-diethylisoxazolidine-3,5-dione as a solid residue. Recrystallization of the solid from methanol gave pure 2-(4-methylbenzoyl)-4,4-diethylisoxazolidine-3,5-dione as a white solid: mp 92°-93° C.; IR (Nujol) 1805 (s,C=O), 1747 (s, C=O), 1695 cm$^{-1}$ (s, C=O);H$^1$ NMR (400 MHz, CDCl$_3$) δ7.70 (d,2H), 7.29 (d,2H), 2.43 (s,3H), 1.95 (q. 4H), 1.00 (t, 6H); High resolution MS, calc'd for: C$_{15}$H$_{17}$NO$_4$: 275.1157. Found: 275.1163. Anal. Calc'd for: C$_{15}$H$_{17}$NO$_4$: C, 65.44; H, 6.23; N, 5.09. Found: C, 65.24; H, 6.45; N, 5.28.

EXAMPLE 6

Preparation of 2-(4-Chlorobenzoyl)-4,4,diethylisoxazolidine-3,5-dione

A mixture consisting of 2.70 g (0.0157 mol) of 4-chlorobenzohydroxamic acid, mp 170°-171° C. (dec). (lit. mp 168° C. dec., Bielstein Handbook of Organic Chemistry, series H, vol 9. p. 341), 5 ml of pyridine, and 100 ml of methylene chloride was prepared in a 250 ml round bottom flask. The mixture was cooled in an ice bath, and 3.097 g (0.0157 mol) of diethylmalonyl chloride was added dropwise over a 15 minutes period with stirring. The reaction mixture was stirred for 4 hours at room temperature after which time all the hydroxamic acid had dissolved. The solution was extracted two times with 50 ml portions of water, three times with 50 ml portions of 5% hydrochloric acid, and two times with 50 ml portions for 5% sodium carbonate. The methylene chloride was dried (MgSO$_4$) and evaporated to dryness under reduced pressure to give 0.76 g (16.4%) of crude 2-(4-chlorobenzoyl)-4,4-diethylisoxazolidine-3,5-dione as a solid residue. Recrystallization of the solid from methanol gave pure 2-(4-chlorobenzoyl)-4,4-diethylisoxazolidine-3,5-dione as a white solid: mp 98°-100° C.; IR (Nujol) 1812 (s, C=O), 1745 (s, C=O), 1700 cm$^{-1}$ (s, C=O); $^1$H NMR (400 MHz, CDCl$_3$) 7.77-7.80 (m, 2H), 7.49-7.52 (m, 2H), 1.99 (q. 4H), 1.04 (t, 6H); High resolution MS, calc'for: C$_{14}$H$_{14}$NO$_4$Cl: 295.0612. Found: 295.0615. Anal. Calc'd for: C$_{14}$H$_{14}$NO$_4$Cl: C, 56.86; H, 4.77; N, 4.74; Cl, 11.99. Found: C, 57.04; H, 4.63; N, 4.58; Cl, 11.88.

EXAMPLE 7

Preparation of 2-(3,4-Dimethoxybenoyl)-4,4-diethylisoxazolidine-3,5-dione

A mixture consisting of 1.97 g (0.0100 mol) of 3,4-dimethoxybenzohydroxamic acid, mp 170°-173° C. (dec.) (lit, mp 167°-168° C., F. Aljundi, E. Hannig, and K. Bohm, *Pharmazie*, 28, 362 (1973)), 5 ml of pyridine, and 100 ml of methylene chloride was prepared in a 250 ml round bottom flask. The mixture was cooled in an ice bath, and 1.977 g (0.0100 mol) of diethylmalonyl chloride was added dropwise over a 15 minute period with stirring. The reaction mixture was stirred for 1 hour at room temperature after which time all the hydroxamic acid has dissolved. The solution was extracted three times with 50 ml portions of water, four times with 50 ml portions of 5% hydrochloric acid, and two times with 50 ml portions of 5% sodium carbonate. The methylene chloride was dried (MgSO$_4$) and evaporated to dryness under reduced pressure to give 2.36 g (73.5%) of crude 2-(3,4-dimethoxybenzoyl)-4,4-diethylisoxazolidine-3,5-dione as a solid residue. Recrystallization of the solid from absolute ethanol gave pure 2-(3,4-dimethoxybenzoyl)-4,4-diethylisoxazolidine-3,5-dione as a white solid: mp 108°–109° C.; IR (Nujol) 1805 (s, C=O), 1752 (s, C=O), 1693 cm$^{-1}$ (s, C=O); $^1$H NMR (400 MHz, CDCl$_3$) $\delta$7.40–7.54 (m, 2H), 6.94–6.96 (d, 1H), 3.98 (s, 3H), 3.94 (s, 3H), 1.97 (q, 4H), 1.02 (t, 6H); High resolution MS, calc'd for: C$_{16}$H$_{19}$NO$_6$: 321.1212. Found: 321.1208. Anal. Calc'd for: C$_{16}$H$_{19}$NO$_6$: C, 59.80; H, 5.96; N, 4.36. Found: C, 60.04; H, 6.05; N, 4.44.

EXAMPLE 8

Preparation of 2-(1-Phenylethenyl)-4,4-diethyl isoxazolidine-3,5-dione

A. In the Presence of Excess Triethylamine

A solution of 5.40 g (0.0400 mol) acetophenone oxime and 11.4 g (0.113 mol) of triethylamine in 200 ml of diethyl ether, which had been dried over lithium aluminum hydride, was prepared in a 500 ml three-neck flask. The flask was fitted with an addition funnel, a condenser, and a calcium chloride drying tube. The solution was cooled to 0° C. in an ice-water bath with stirring. A solution containing 7.94 g (0.0400 mol) of diethylmalonyl chloride in 100 ml of dry diethyl ether was added dropwise over a one-hour period. The solution was stirred at room temperature for 24 hours. The white precipitate was removed by suction filtration to give 1.0 g (91%) of triethylamine hydrochloride mp 260°–3° C. (dec.). The clear yellow filtrate was extracted three times with 200 ml of 10% hydrochloric acid, dried (MgSO$_4$), and concentrated under reduced pressure to give 9.95 g of a clear brown oil: IR(neat) 2958(m), 2924(m), 2855(w), 1810(w), 1752(s), and 1670(s) cm$^{-1}$.

The crude product residue was allowed to stand at room temperature for 48 hours. White granular crystals precipitated. They were separated from the brown oil by dissolving the oil in 50 ml of chlorofrom:hexane (25:75) and recrystallized from 20 ml of hot petroleum ether to give 0.87 g (10%) of 1,1-bis-[2-(4,4-diethylisoxazolidine-3,5-dione)]-1-phenylethane: mp 143°–145° C.; IR (Nujol) 3180(w), 3020(w), 1760(s), and 1672 (s)cm$^{-1}$; UV max (CH$_3$OH) 250 nm ($\epsilon$10,100); $^1$H NMR (CDCl$_3$) $\delta$10.25 (s, broad), 7.43(m), 3.75 (overlapping s), 2.03(q), 1.63(q), 1.06(t) and 0.47(t); high resolution MS, calc'd for: C$_{15}$H$_{18}$NO$_3$: 260.1286; found: 260.1286; Ms m/z (rel. intensity) 260 (3), 247 (45), 246 (100), 219 (52), and 105 (99).

The chloroform:hexane solution was concentrated under reduced pressure to give 8.60 g of a brown oil containing 2-(1-phenylethenyl)-4,4-diethylisoxazolidine-3,5-dione: IR(neat) 3205(w), 3085(w), 3063(w), 3038(w), 2975(m), 2940(m), 2884(w), 1835(w), 1748(s) and 1686 cm$^{-1}$(s); $^1$H NMR (CDCl$_3$) $\delta$7.35(m), 5.54 (s, vinyl CH), 5.43 (s,vinyl CH), 3.47(s), 3.40(s), 2.60(s), 2.38(s) 1.90 (complex, m), and 1.00 (complex, m).

B. In the Presence of a Stoichiometric Amount of Triethylamine

A solution of 2.70 g (0.0200 mol) or acetophenone oxime and 4.04 g (0.0400 mol) of triethylamine in 150 ml of diethyl ether, which had been dried by distillation over lithium aluminum hydride, was prepared in a 500 ml three-neck flask. The flask was fitted with an addition funnel, a condenser, and a calcium chloride drying tube. A solution containing 3.92 g (0.0200 mol) of diethylmalonyl chloride in 100 ml of dry diethyl ether was added dropwise over a one-hour period. The reaction solution was stirred at room temperature for 24 hours. The white precipitate was removed by suction filtration to give 5.2 g (94.5%) of triethylamine hydrochloride: mp 260°–263° C. The clear yellow filtrate was concentrated under reduced pressure to give 4.8 g of a clear brown oil containing 2-(1-phenylethenyl)-4,4-diethyl isoxazolidine-3,5-dione: IR(neat) 3260 (br, w), 2915(m), 2890(m), 2835(w), 1805(s) 1720(s), and 1620 cm$^{-1}$(s); $^1$H NMR (CDCl$_3$) $\delta$7.4 (s overlapping in weak m), 5.6(s), 5.5(s), 2.3(s), 2.2(s), 1.9(q), and 1.0(t).

Purification of 2-(1-Phenylethenyl)-4,4-diethylisoxazolidine-3,5-dione by Column Chromatography Analysis of crude 4,4-diethyl-2-(1phenylethenyl) isoxazolidine 3,5-dione was performed by thin layer chromatography (TLC) on Bakerflex Silica Plates using methylene chloride:hexane (98:2) as the mobile phase. Components appeared at R$_f$ 0.80, 0.78, 0.72, 0.60, 0.52, and 0.0. A sample of the crude isoxazolidine-3,5-dione weighing 3.50 g (38.4% purity by HPLC) was dissolved in 5.0 ml of chloroform:hexane (98:2), and applied to a 37×2 cm (O.D.) chromatography column containing 60–200 mesh silica gel as the adsorbant. The eluting solvent was chloroform:hexane (98:2) and the elution rate was 1 ml/min. Twenty 50 ml fractions were collected and analyzed by TLC as described above. Fractions 11, 12, 13 and 14 showed a single component, R$_f$ 0.60. These fractions were combined and concentrated to give 1.0 g of pure 4,4-diethyl-2-(1-phenylethenyl-)isoxazolidine-3,5-dione as a viscous oil: IR(neat) 2976(w), 2938(w), 2882(w), 1816(s), 1721(s) and 1626 (s)cm$^{-1}$; UV max (CH$_3$OH) 245 nm ($\epsilon$6800); $^1$H NMR (CDCl$_3$) $\delta$7.72 (s, overlapping a small m, 5, aromatic CH) 5.47 (s, 1, vinyl CH), 5.34 (s, 1, vinyl CH), 1.83 (q, 4, CH$_2$) and 0.91 (t, 6, CH$_3$); high resolution MS, calc'd for: C$_{15}$H$_{17}$NO$_3$: 259.1208. Found: 259.1209; MS m/z (rel. intensity) 259 (44), 215 (48), 199 (85), 108 (89) and 106 (100). *Elemental Analysis:* Calc'd for: C$_{15}$H$_{17}$NO$_3$:C, 69.48; H, 6.61; N, 5.40. Found: C,69,64; H, 6.91; N, 5.04.

EXAMPLE 9

Preparation of 1,1-bis-[2-(4,4-Diethylisoxazolidine-3,5-dione)]cyclohexane

A. In the Presence of Excess Triethylamine

A solution of 2.26 g (0.0200 mol) of cyclohexanone oxime and 6.06 g (0.0600 mol) of triethylamine in 150 ml of diethyl ether, which has been dried by distillation over lithium aluminum hydride, was prepared in a 500 ml three-neck flask. The flask was fitted with an addition funnel, a condenser, and a calcium chloride drying tube. The solution containing 3.92 g (0.0199 mol) of diethylmalonyl chloride in 100 ml of dry diethyl ether was added dropwise over a one-hour period. The solution was stirred at room temperature for 24 hours. The white precipitate was removed by suction filtration to give 5.01 g (91.1%) of triethylamine hydrochloride: mp 260°–263° C. dec. The clear yellow filtrate was extracted three times with 200 ml of 10% hydrochloric acid, dried (MgSO$_4$), and concentrated to give 3.4 g of a clear brown oil: IR(neat) 2952(s), 1817(s), 1728(s), and 1130(m) cm$^{-1}$; $^1$H NMR (CDCl$_3$) $\delta$5.9(m), 2.7–1.4(m), and 0.90(t). The crude product was allowed to stand at room temperature for 24 hours. White granular crystals gradually precipitated. The oil was dissolved in 30 ml of methanol, and the crystals were collected by suction filtration to give 0.34 g (8.6%) of 1,1-bis-[2-(4,4-diethylisoxazolidine-3,5-dione)]cyclohexane: mp 102°-103° C.; IR (Nujol) 1810(s), 1715(s), and 1120 cm$^{-1}$(m); $^1$H NMR (CDCl$_3$) δ2.58 (m, 4), 2.2-1.2(m, 14), and 0.95 (t, 12). *Elemental Analysis:* Calc'd for: C$_{20}$H$_{30}$N$_2$O$_6$: C, 60.89, H, 7.67. Found: C, 60.91; H, 7.62.

B. In the Presence of a Stoichiometric Amount of Triethylamine

A solution of 2.26 g (0.0200 mol) of cyclohexanone oxime and 4.40 g (0.0400 mol) of triethylamine in 150 ml of diethyl ether, which had been dried by distillation over lithium aluminum hydride, was prepared in a 500 ml three-neck flask. The flask was fitted with an addition funnel, a condenser, and a calcium chloride drying tube. The solution was cooled to 0° C. in an ice-water bath with stirring. A solution containing 3.92 g (0.0199 mol) of diethylmalonyl chloride in 100 ml of dry diethyl ether was added dropwise over a one-hour period. The reaction solution was stirred at room temperature for 24 hours. The white precipitate was removed by suction filtration to give 5.00 g (90.9%) of triethylamine hydrochloride: mp 260°-263° dec. The clear yellow filtrate was concentrated under reduced pressure to give 3.7 g of a clear brown oil: IR(neat) 1935(s), 2865(m), 1706(s), and 1120 (m)cm$^{-1}$; $^1$H NMR (CDCl$_3$) δ5.93(m), 2.8-1.2(m) 1.75(q), and 1.93(t). Analysis by HPLC was performed on a Whatman Partisil-10, ODS-2, 25 CM, reverse-phase column using a detector wavelength of 254 nm, a solvent flow rate of 3.0 ml/min., and a solvent system of water:acetonitrile (40:60). Peaks appeared at $t_R$ 0.80 (33.1%), 2.05 (0.6%), 1.50 (2.3%), 4.35 (55.4%) and 8.15 (8.6%) minutes. The crude oil was allowed to stand at room temperature for 24 hours. White granular crystals gradually precipitated. The oil was dissolved in methanol and the crystals were collected by suction filtration to yield 0.50 g (13%) of 1,1-bis-[2-(4,4-diethylisoxazolidine-3,5-dione)]cyclohexane as white crystals: mp 102°-103° C. The white crystals were recrytalized from 10 ml of low boiling petroleum ether to give 0.46 g of pure 1,1-bis-[2-(4,4-diethylisoxazolidine-3,5-dione)]cyclohexane: mp 102°-103° C.; 1R (CHCl$_3$) 1810(s) and 1715 (s)cm$^{-1}$; UV max (CH$_3$OH) 226 nm (ε2500); $^1$H NMR (CDCl$_3$) δ2.63(m,4), 2.2-1.2(m,14), and 0.95(t,12); high resolution MS, calc'd for: C$_{13}$H$_{20}$NO$_3$: 238.1443; found: 238.1444; MS m/z (rel. intensity) 238 (66%), 193 (10%), 164 (11%), 98 (26%), 97 (57%), 95 (100%). The brown methanol solution was concentrated under reduced pressure to give 3.1 g of a clear brown oil containing 2-(1-cyclohexenyl)-4,4-diethylisoxazolidine-3,5-dione: IR(neat) 2915(s), 1818(s), 1715(s), and 1128(m) cm$^{-1}$; $^1$H NMR (CDCl$_3$) 6.16 (broad,s), 3.1(s), 2.6(m), 2.2-1.2(m), 1.1-0.6(m). Analysis was performed by HPLC using the conditions described above to give peaks at $t_R$ 0.80 (42.6%), 1.95 (0.8%), 4.30 (46.8%), and 8.25 (9.7%) minutes.

EXAMPLE 10

Testing of Normal Mice

The ten compounds listed in Table II below were tested for their hypolipidemic activity in CF$_1$ mice.

TABLE II

| Compound No. | Name |
|---|---|
| A | 2-(2-propenyl)-4,4-diethylisoxazolidine-3,5-dione |
| B | 2-(1-phenylethenyl)-4,4-diethylisoxazolidine-3,5-dione |
| C | 1,1-bis-[2-(4,4-diethylisoxazolidine-3,5-dione)]cyclohexane |
| D | 2-(3,4,5-trimethoxybenzoyl)-4,4-diethylisoxazolidine-3,5-dione |
| E | 2-benzoyl-4,4-diethylisoxazolidine-3,5-dione |
| F | 2,2-bis-[2-(4,4-diethylisoxazolidine-3,5-dione)]propane |
| G | 2-(3,4-dimethoxybenzoyl)-4,4-diethylisoxazolidine-3,5-dione |
| H | 2-(4-methoxybenzoyl)-4,4-diethylisoxazolidine-3,5-dione |
| I | 2-(4-methylbenzoyl)-4,4-diethylisoxazolidine-3,5-dione |
| J | 2-(4-chlorobenzoyl)-4,4-diethylisoxazolidine-3,5-dione |

Compounds A-J as defined above, were suspended in an aqueous 1 percent carboxymethylcelulose (CMC) solution and homogenized. Each of the so prepared compounds were administered to a group of six CF$_1$ male mice, each weighing approximately 25 grams, intraperitioneally for 16 days. Each of these compounds were provided in a dosage of 20 mg/kg/day ip. On Days 9 and 16 blood was obtained by tail vein bleeding. The blood serum so obtained was separated by centrifugation for three minutes. Serum cholesterol levels were determined by a modification of the Liebermann-Burchard reaction (Ness, *Clin. Chim. Acta.*, Vol. 10, 229 [1964]). Serum triglyceride levels were determined on Day 16 by use of the Fisher, Hycel Triglyceride Test Kit.

In addition to the above-described treated mice, an untreated control group of six mice were similarly tested on Days 9 and 16 to determine their serum cholesterol and trigylceride blood levels. Based on the results obtained for the untreated control group, the percent control, based on serum cholesterol and serum triglyceride levels of the treated mice compared to the untreated mice, was obtained. Table III reports this percent control, including standard deviation, indicating the level of confidence of these numbers.

TABLE III

| | Serum Cholesterol* | | Serum Triglyceride |
|---|---|---|---|
| Compound No. | Day 9 | Day 16 | Day 16 |
| A | 70 ± 7 | 75 ± 4 | 71 ± 6 |
| B | 71 ± 5 | 63 ± 6 | 71 ± 4 |
| C | 86 ± 7 | 73 ± 7 | 77 ± 9 |
| D | 82 ± 6 | 51 ± 5 | 66 ± 6 |
| E | 77 ± 5 | 53 ± 6 | 63 ± 7 |
| F | 95 ± 4 | 57 ± 6 | 68 ± 8 |
| G | 81 | 77 | 84 |
| H | 89 | 62 | 63 |
| I | 73 | 46 | 86 |
| J | 64 | 45 | 76 |
| 1% Carbonymethycellulose | 100 ± 6 | 100 ± 5 | 100 ± 7 |

*Reported as a percentage of serum cholesterol or serum triglyceride level as control + or − the standard deviation.

EXAMPLE 11

Testing of Hyperlipidemic Mice

A group of six CF$^1$ male mice (about 25 g) was placed on a commercial diet (U.S. Biochemical Corporation BAsal Atherogenic Test Diet) which produced a "hyperlipidemic" state. That is, the average serum cholesterol level in the group of treated mice was raised from 122 to 375 mg % and triglyceride levels were raised from 137 to 367 mg/dl.

Upon reaching these hyperlipidemic levels, the mice were administered Compound D in a concentration of 20 mg/kg/day intraperitoneally for 14 days while continuing the diet. On Day 14, serum cholesterol and serum triglyceride levels were measured in accordance with the procedure of Example 10. The serum cholesterol level was found to be lowered by 40% from 375 mg % to 150 mg % while the serum triglyceride level was reduced by 51% from 367 mg/dl to 187 mg/dl.

EXAMPLE 12

Serum Testing of Normal Rats

A test solution of Compound D, 2-(3,4,5-trimethoxybenzoyl)-4,4-diethylisoxazolidine-3,5-dione, was suspended in an aqueous solution of 1% CMC, homogenized and administered orally to six Sprague-Dawley male rats, which each weighed approximately 350 grams. Similarly, six Sprague-Dawley male rats of approximately the same weight were administered similar volumes of the same aqueous 1% CMC solution without the active agent, Compound D, also orally. In each case, administration was by intubation needle at 20 mg/kg/day for 14 days. In addition, as a control, a similar group of six male Sprague-Dawley rats were untreated.

On Days 7 and 14, blood was obtained from each of the rats of the three groups by tail vein bleeding. The blood obtained was separated by centrifugation for three minutes. Serum cholesterol and triglyceride levels were determined in accordance with the procedure of Example 10.

The results of this test indicated that the serum cholesterol levels of the rats treated with the inert agent, the 1 percent CMC solution, was 100 percent both on Day 7 and on Day 14 when compared to the serum cholesterol level of the control rats. However, the rats treated with Compound D of the present invention were found to have a serum cholesterol level of 77 percent on Day 7, and of 61 percent on Day 14 when compared to the average serum cholesterol level of the control rats.

The serum triglyceride test demonstrated a serum triglyceride concentration of 100 percent for the group of rats treated with the aqueous 1 percent CMC solution on Day 7 and a serum triglyceride level of 100 percent on Day 14 compared to the average serum triglyceride concentration of the control rats.

The rats treated with a concentration of 20 mg/kg/day of Compound D of the present invention had an average serum triglyceride level of 64 percent on Day 7 and a serum triglyceride level of 43 percent on Day 14 compared to the serum triglyceride average level of the control mice.

EXAMPLE 13

Formulations

A. TABLET

| Ingredient | Amount per tablet |
|---|---|
| Compound D | 150.0 mg |
| Lactose | 100.0 mg |
| Corn Starch | 15.0 mg |
| Magnesium stearate | 1.0 mg |

The active compound is finely ground and intimately mixed with the powdered excipients (lactose, corn starch, and magnesium stearate). The formulation is then compressed in a die to produce the tablet.

B. COATED TABLET

| Ingredient | Amount per tablet |
|---|---|
| Core | |
| Compound D | 150.0 mg |
| Corn Starch | 25.0 mg |
| Magnesium stearate | 2.0 mg |
| Coating | |
| Lactose | 200.0 mg |
| Corn Starch | 50.0 mg |
| Gelatin | 10.0 mg |

The active ingredient and starch are granulated with water and dried. Magnesium stearate is added to the dried granules. Lactose and starch are granulated with 10% w/v aqueous solution of gelatin and dried. Magnesium stearate is added to the dried coating granules. The granulated core is compressed with the granulated coating in a conventional compression molding press.

C. CAPSULE

| Ingredient | Amount per Capsule |
|---|---|
| Compound D | 150.0 mg |
| Lactose | 200.0 mg |
| Magnesium stearate | 10.0 mg |

The finely ground active compound is mixed with the powdered excipients and packed into a two part gelatin capsule.

D. SUSPENSION

| Ingredient | Amount per ml |
|---|---|
| Compound D | 75.0 mg |
| Sodium lauryl sulfate | 25.0 mg |
| Hydroxypropylmethylcellulose | 100.0 mg |
| Sucrose | 50.0 mg |
| Flavor and Color | q.s. |
| Water | q.s. 1.0 ml |

The sodium lauryl sulfate, hydroxypropylmethylcellulose, flavor and color are triturated with the active compound. This mixture is then blended with 0.5 ml water and sucrose, and additional water is added to make the total volume 1.0 ml of suspension.

Toxicity Studies

The toxicity studies performed to date demonstrated $LD_{50}$ values $>500$ mg/kg in $CF_1$ male mice (approx. 25 g).

What we claim is:

1. An isoxazolidine-3,5-dione having hypolipidemic activity and the structural formula:

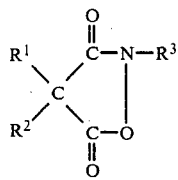

wherein

R¹ and R² are each an alkyl of 1 to 4 carbons;

R³ is an alkoxybenzoyl group containing from 1 to 3 alkoxy groups wherein the alkoxy groups have from 1 to 4 carbon atoms, an alkylbenzoyl group wherein the alkyl group has from 1 to 4 carbons, a halobenzoyl group, or a group

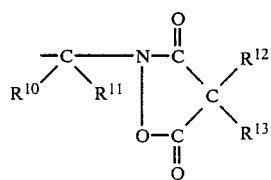

where together $R^{10}$ and $R^{11}$ form a $C_3$ to $C_7$ alkylene group, and $R^{12}$ and $R^{13}$ are each an alkyl from 1 to 4 carbon atoms, the pharmaceutically acceptable salts, and mixtures thereof.

2. The compound of claim 1 selected from the group consisting of:
   1,1-bis-[2-(4,4-diethylisoxazolidine-3,5-dione)]cyclohexane;
   2-(3,4,5-trimethoxybenzoyl)-4,4-diethylisoxazolidine-3,5-dione;
   2-(3,4-dimethoxybenzoyl)-4,4-diethylisoxazolidine-3,5-dione;
   2-(4-methoxybenzoyl)-4,4-diethylisoxazolidine-3,5-dione;
   2-(4-methylbenzoyl)-4,4-diethylisoxazolidine-3,5-dione; and
   2-(4-chlorobenzoyl)-4,4-diethylisoxazolidine-3,5-dione.

3. The compound of claim 1 selected from the group consisting of
   2-(3,4,5-trimethoxybenzoyl)-4,4-diethylisoxazolidine-3,5-dione;
   2-(4-methylbenzoyl)-4,4-diethylisoxazolidine-3,5-dione; and
   2-(4-chlorobenzoyl)-4,4-diethylisoxazolidine-3,5-dione.

4. The compound 2-(3,4,5-trimethoxybenzoyl)-4,4-diethylisoxazolidine-3,5-dione.

* * * * *

UNITED STATES PATENT AND TRADEMARK OFFICE
CERTIFICATE OF CORRECTION

PATENT NO. : 4,946,963

DATED : August 7, 1990

INVENTOR(S) : Izydore, Robert A.; Hall, Iris H.

It is certified that error appears in the above-identified patent and that said Letters Patent is hereby corrected as shown below:

IN COLUMN 1:

ON line 8, before "Background of The Invention", insert --This invention was made with Government Support under a grant awarded by the National Institutes of Health.--.

Signed and Sealed this

Twenty-eighth Day of July, 1992

Attest:

DOUGLAS B. COMER

Attesting Officer    Acting Commissioner of Patents and Trademarks